United States Patent
Scarlett et al.

(10) Patent No.: US 6,265,624 B1
(45) Date of Patent: Jul. 24, 2001

(54) PROCESS FOR PREPARING PENTANE-1,5-DIOL

(75) Inventors: John Scarlett, Kirk Merrington; Michael Anthony Wood, Yarm; Paul Willett, Witton le Wear, all of (GB)

(73) Assignee: Kvaerner Process Technology, Ltd., London (GB)

( * ) Notice: Subject to any disclaimer, the term of this patent is extended or adjusted under 35 U.S.C. 154(b) by 0 days.

(21) Appl. No.: 09/553,255

(22) Filed: Apr. 19, 2000

(30) Foreign Application Priority Data

Apr. 27, 1999 (EP) .................................................. 99303236

(51) Int. Cl.$^7$ ............................. C07C 31/18; C07C 27/26
(52) U.S. Cl. ........................................... 568/853; 568/854
(58) Field of Search ..................................... 568/853, 854

(56) References Cited

PUBLICATIONS

Abstract of Japanese Patent Publication No. 01085937 published Mar. 30, 1989, 1 page.

J. Schossig, et al., "Alcohols, Polyhydric", Ullmann's Encyclopedia of Industrial Chemistry, 5th Edition, vol. A1, pp. 305–320, 1985.

*Primary Examiner*—Amelia Owens
(74) *Attorney, Agent, or Firm*—Senniger, Powers, Leavitt & Roedel

(57) ABSTRACT

A process is described for the continuous recovery of substantially pure pentane-1,5-diol from a crude product stream (1) containing pentane-1,5-diol and δ-valerolactone. The feed stream (1) is continuously supplied to a vaporization zone (2) maintained under temperature and pressure conditions effective for the vaporization of pentane-1,5-diol and conducive to the thermal decomposition of reaction products of δ-valerolactone thereby to form a vaporous stream. The resulting vaporous stream is continuously supplied to an intermediate section of a distillation zone (4). A reflux stream (5) of dimethyl glutarate is fed to an upper section of the distillation zone (4) and an overhead vapor product stream (8) comprising δ-valerolactone and dimethyl glutarate is taken. Also an intermediate stream (11) comprising substantially pure pentane-1,5-diol is taken from the distillation zone (4), while from the bottom section of the distillation zone there is recovered a bottoms product (12).

8 Claims, 1 Drawing Sheet

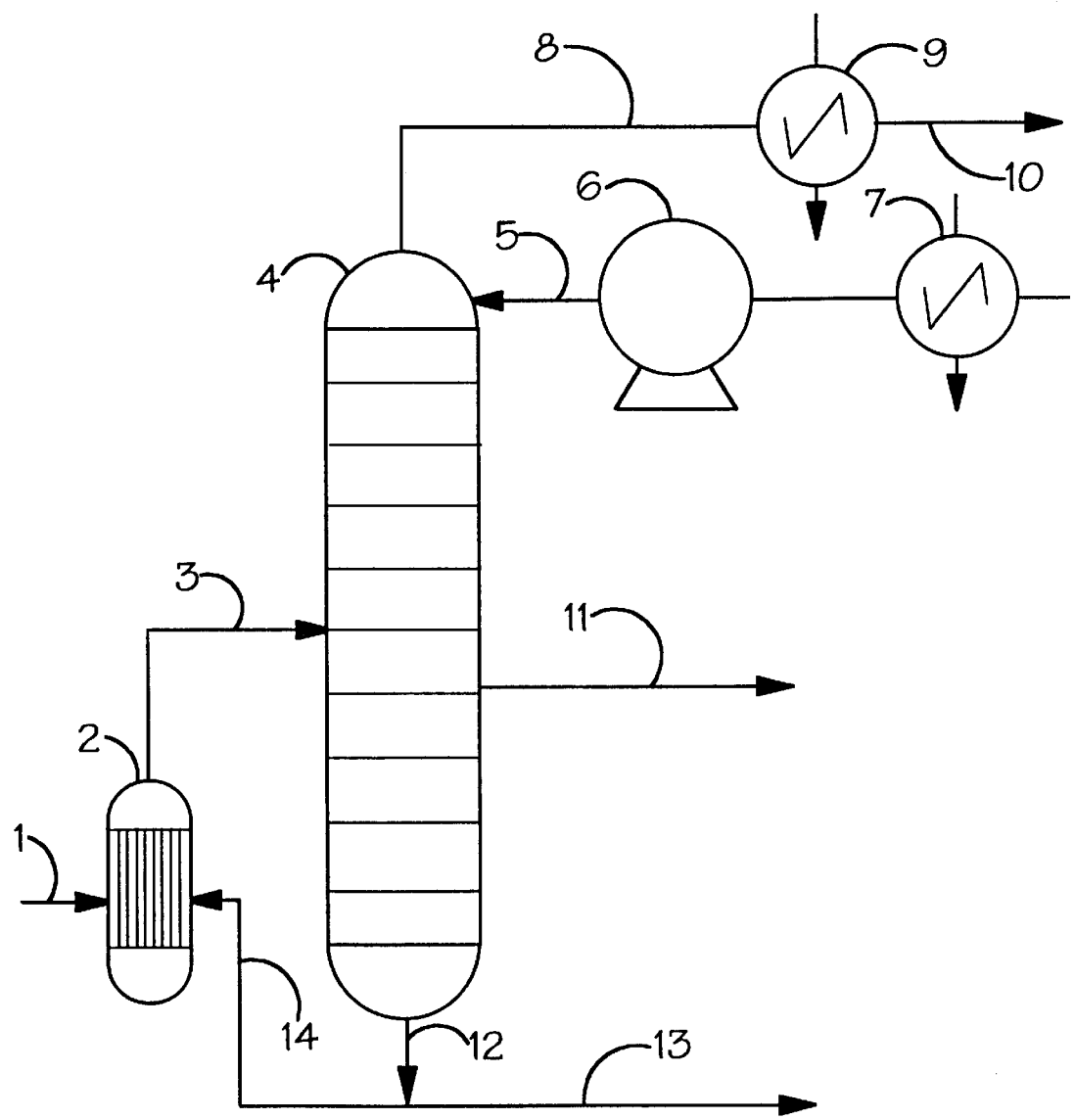

PROCESS FOR PREPARING PENTANE-1,5-DIOL

This invention relates to a process for the production of pentane-1,5-diol.

Pentane-1,5-diol (or pentamethylenediol) has the formula:

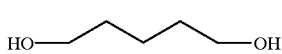

(1)

It is a specialty chemical which has potential for use in the plastics industry as a monomer from which to make polyesters. Pentane-1,5-diol is commercially available at a purity of 96% with a quoted boiling point of 242° C.

One method of producing pentane-1,5-diol is by hydrogenation of a dialkyl glutarate, such as dimethyl glutarate, according to the following equation:

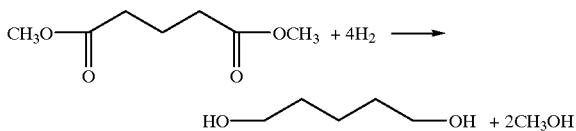

(2)

However, a byproduct of this reaction is δ-valerolactone of the formula:

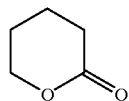

(3)

which is a reactive compound. Thus δ-valerolactone can polymerise to form a polymer of the formula:

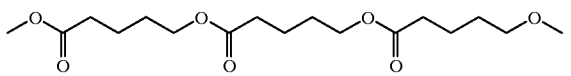

(4)

Such polymers cause difficulties in the purification of pentane-1,5-diol because they tend to break down during distillation, thereby reforming δ-valerolactone. Another possible reaction is that between the alkanol, e.g. methanol, present in the crude hydrogenation product to form methyl 5-hydroxypentanoate according to the reaction:

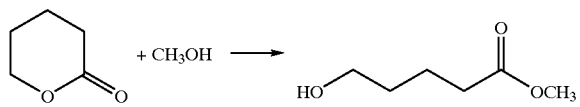

(5)

These reaction products tend to form spontaneously even at ambient temperature and slowly decompose during distillation of the crude pentane-1,5-diol, thereby reforming δ-valerolactone. In addition conditions in a distillation column can favour the formation of polyesters and other heavy byproducts, including methyl 5-hydroxypentanoate. According to the published literature δ-valerolactone is commercially available at a purity of 99%. Such a commercial product has a quoted melting point of 38° C. to 40° C. and a boiling point of 256° C. Since the boiling point of δ-valerolactone is close to that of pentane-1,5-diol, its separation from pentane-1,5-diol during distillation of the crude hydrogenation product is problematic because δ-valerolactone behaves non-ideally during distillation and tends to report with pentane-1,5-diol in the distillation step. Hence it is difficult to avoid small amounts of δ-valerolactone contaminating the pentane-1,5-diol distillation product.

It would accordingly be desirable to provide a process for the purification of crude pentane-1,5-diol from a crude hydrogenation product containing same, for example a crude hydrogenation product resulting from the hydrogenation of a dialkyl glutarate, such as diethyl glutarate or, preferably, dimethyl glutarate. It would further be desirable to provide such a process that can be operated continuously.

The present invention accordingly seeks to provide a process for the purification of a crude pentane-1,5-diol which contains minor amounts of δ-valerolactone so as to produce a pentane-1,5-diol product that is substantially free from δ-valerolactone. It further seeks to provide a process for the recovery from a crude product containing pentane-1,5-diol and δ-valerolactone of substantially pure pentane-1,5-diol. Yet another objective of the invention is to provide a continuous process for the recovery of pentane-1,5-diol from a crude product containing both pentane-1,5-diol and δ-valerolactone.

According to one aspect of the present invention there is provided a process for the continuous recovery of substantially pure pentane-1,5-diol from a crude product stream containing pentane-1,5-diol and δ-valerolactone which comprises:

continuously supplying the feed stream to a vaporisation zone maintained under temperature and pressure conditions effective for the vaporisation of pentane-1,5-diol and conducive to the thermal decomposition of reaction products of δ-valerolactone thereby to form a vaporous stream;

continuously supplying resulting vaporous stream to an intermediate section of a distillation zone, said intermediate section lying below an upper distillation section and above a lower distillation section;

continuously supplying to the upper section of the distillation zone a reflux stream of dimethyl glutarate;

continuously recovering from the upper section of the distillation zone an overhead vapour product stream comprising δ-valerolactone and dimethyl glutarate;

continuously recovering from the distillation zone an intermediate stream comprising substantially pure pentane-1,5-diol; and continuously recovering from the bottom section of the distillation zone a bottoms product.

In a preferred process the bottoms product is recycled to the vaporisation zone.

It will thus be appreciated that the process of the invention involves the use of a vaporisation zone which precedes and is separate from the distillation zone. By use of such an arrangement it can effectively be ensured that reaction products from δ-valerolactone do not enter the distillation zone but remain in the sump section of the vaporisation zone. Thus, although the vapour stream supplied to the distillation zone contains δ-valerolactone, it cannot reform undesirable products and thus does not behave in a non-ideal way. Hence the separation of traces of δ-valerolactone from the pentane-1,5-diol product is facilitated.

The dimethyl glutarate used as reflux stream has a higher boiling point than δ-valerolactone and hence helps to ensure that in the distillation zone δ-valerolactone remains vaporous and hence cannot condense and form undesirable condensation products.

Dimethyl glutarate has a published boiling point of 93° C. to 95° C. at 13 mm Hg (1733.19 kpa), i.e. a boiling point lower than pentane-1,5-diol, and hence, when it is used as the material of the reflux stream, it reports in the vaporous overhead stream from the upper section of the distillation zone. This vaporous overhead stream can then be condensed. When the process used for the production of pentane-1,5-diol involves hydrogenation of dimethyl glutarate, then the resulting condensate can recycled to the hydrogenation zone to form the feed, or a part of the feed, thereto.

Hence according to another aspect of the present invention there is provided a process for the continuous production of pentane-1,5-diol which comprises:

supplying a feed stream comprising dimethyl glutarate in admixture with hydrogen to a hydrogenation zone containing a charge of an ester hydrogenation catalyst maintained under temperature and pressure conditions effective for the hydrogenation of dimethyl glutarate to pentane-1,5-diol;

recovering from the hydrogenation zone a hydrogenation product mixture comprising unreacted hydrogen, methanol, δ-valerolactone and pentane-1,5-diol;

separating from the hydrogenation product mixture a crude reaction product stream comprising δ-valerolactone and pentane-1,5-diol;

continuously supplying the crude reaction product stream to a vaporisation zone maintained under temperature and pressure conditions effective for the vaporisation of pentane-1,5-diol and conducive to the thermal decomposition of reaction products of δ-valerolactone thereby to form a vaporous stream;

continuously supplying resulting vaporous stream to an intermediate section of a distillation zone, said intermediate section lying below an upper distillation section and above a lower distillation section;

continuously supplying to the upper section of the distillation zone a reflux stream of dimethyl glutarate;

continuously recovering from the upper section of the distillation zone an overhead vapour product stream comprising δ-valerolactone and dimethyl glutarate;

continuously recovering from the distillation zone an intermediate stream comprising substantially pure pentane-1,5-diol;

continuously recovering from the bottom section of the distillation zone a bottoms product; and recycling material of the overhead vaporous stream from the distillation zone to the hydrogenation zone.

In such a process the hydrogenation catalyst is preferably a reduced copper chromite catalyst, for example, that sold under the designation DRD92/89 by Kvaerner Process Technology Limited of P.O. Box P.O. Box 37, Bowesfield Lane, Stockton-on-Tees, Cleveland TS18 3HA. Typical reaction conditions include use in the hydrogenation zone of a hydrogen:dimethyl glutarate molar ratio of from about 200:1 to about 600:1, a temperature in the range of from about 180° C. to about 250° C., and a total pressure of from about 450 psig to about 1000 psig (about 3102 kpag to about 6894 kpag).

Preferably the vaporisation zone and the distillation zone are operated at substantially the same pressure. The pressure of operation is preferably atmospheric (e.g. about 101.325 kPa) or sub-atmospheric, e.g. a pressure in the range of from about 100 Pa up to about 100 kPa, more preferably in the range of from about 1 kPa up to about 60 kPa, and even more preferably at a pressure in the range of from about 2 kPa up to about 20 kPa. The temperature of operation of the vaporisation zone is selected in accordance with the pressure of operation so as to cause pentane-1,5-diol to boil and thus ensure that a vaporous overhead stream is formed comprising pentane-1,5-diol. Likewise the distillation zone is operated under temperature conditions selected so as to ensure that pentane-1,5-diol boils at the prevailing pressure and hence an overhead vaporous fraction is recovered overhead from the upper section of the distillation zone that contains light end products such as methanol and also δ-valerolactone and dimethyl glutarate, and so that the requisite side stream of substantially pure pentane-1,5-diol is also formed.

In order that the invention may be clearly understood and readily carried into effect a preferred process in accordance with the invention will now be described, by way of example only, with reference to the accompanying diagrammatic drawing which is a flow sheet of a plant designed for recovery of substantially pure pentane-1,5-diol from a crude product containing, in addition to pentane-1,5-diol, also δ-valerolactone.

Referring to the drawing, a crude pentane-1,5-diol stream is supplied in line 1 to a vaporiser 2 which is operated at a pressure of about 6.67 kPa. The crude product in line 1 is, for example, a stream obtained by preliminary distillation of a crude product stream recovered from a hydrogenation zone in which dimethyl glutarate is hydrogenated in the vapour phase over a reduced copper chromite catalyst. Such a crude product stream contains, in addition to pentane-1,5-diol also some δ-valerolactone, as well as methanol. It also contains reaction byproducts caused by reaction of δ-valerolactone with itself or with methanol, i.e. a condensation polymer of δ-valerolactone and/or methyl 5-hydroxypentanoate. From the top of vaporiser 2 there is recovered a vaporous stream in line 3 which comprises pentane-1,5-diol and δ-valerolactone. This is fed to an intermediate section of a distillation column 4. A reflux stream consisting of pure dimethyl glutarate is supplied in line 5 under the influence of pump 6, this stream of dimethyl glutarate having been preheated in heat exchanger 7 to an appropriate temperature. Since dimethyl glutarate has a lower boiling point than pentane-1,5-diol, it appears in the overhead product in line 8 from distillation column 4, together with δ-valerolactone present in the vaporous stream in line 3. The overhead product in line 8 is condensed by means of condenser 9 and is recycled as a part of the feed to the hydrogenation zone (not shown). From a lower part of the distillation column 4 there is recovered a side draw stream consisting of substantially pure pentane-1,5-diol in line 11. A bottoms product is recovered from the bottom of distillation column 4 in line 12. Part is purged from the plant in line 13 while the remainder is recycled in line 14 to the vaporiser 2 which thus replaces the usual reboiler required in a distillation zone.

The invention is further illustrated in the following Examples.

EXAMPLE 1

A mixture of methanol and δ-valerolactone was heated under reflux at a temperature of 65° C. The reaction mixture was analysed by gas chromatography with the results set out in Table 1.

TABLE 1

| Time (hours) | MeOH | HMP | δ-VAL (solid) |
|---|---|---|---|
| 0 | 85.5 | — | 13.89 |
| 3 | 91.8 | 0.9 | 6.0 |
| 5 | 92.0 | 0.9 | 6.3 |
| 8 | 91.4 | 0.6 | 6.7 |
| 12 | 91.5 | 0.6 | 6.9 |
| 16 | 92.1 | 0.5 | 6.7 |
| 19 | 91.2 | 1.1 | 6.7 |

Notes:
MeOH = methanol
HMP = methyl 5-hydroxypentanoate
δ-VAL = δ-valerolactone

EXAMPLE 2

A laboratory scale batch distillation column fitted with a separate vaporiser was used in this Example. Its vaporiser was charged with 1.5 kg of crude pentane-1,5-diol obtained by hydrogenation in the vapour phase of dimethyl glutarate using a reduced copper chromite catalyst. The composition of this feed was as follows:

butane-1,4-diol (BDO) 0.01 wt % pentane-1,5-diol (PDO) 92.35 wt % methyl 5-hydroxypentanoate 1.60 wt % dimethyl glutarate (DMG) 1.53 wt % hexane-1,6-diol (HDO) 0.99 wt % di-(5-hydroxypentyl) ether (DHPE) 0.03 wt %

Preheated dimethyl glutarate was supplied as a reflux stream near the top of the distillation column. After an initial period during which dimethyl glutarate was supplied at a rate which proved to be too high, the rate of supply of dimethly glutarate was reduced to about 10 ml per hour. 10 ml fractions were taken overhead and analysed by gas chromatography with the results summarised in Table 2.

TABLE 2

| Fraction | 10 | 20 | 30 | 40 | 50 | 60 | 70 | 80 | 90 | Pot |
|---|---|---|---|---|---|---|---|---|---|---|
| DMG feed rate (ml/h) | 11 | 11 | 11 | 16 | 11 | 10 | 0 | 0 | 0 | — |
| Pressure (kPa) | 6.67 | 6.67 | 6.67 | 6.67 | 6.67 | 6.53 | 6.67 | 6.67 | 6.67 | — |
| Reflux ratio | 50:1 | 50:1 | 45:1 | 50:1 | 65:1 | 35:1 | T/R | 40:1 | 40:1 | — |
| Pot (° C.) | 169 | 176 | 170 | 170 | 170 | 169 | 170 | 170 | 172 | — |
| Overhead (° C.) | 132 | 134 | 134 | 132 | 133 | 139 | 166 | 166 | 167 | — |
| Analysis wt % | | | | | | | | | | |
| Butane-1,4-diol | 0.01 | 0.14 | 0.29 | 0.14 | 0.01 | N/D | N/D | N/D | N/D | — |
| Pentane-1,5-diol | 0.09 | 11.96 | 8.87 | 0.46 | 11.79 | 10.10 | 96.40 | 99.45 | 99.67 | 92.20 |
| δ-valerolactone | 2.63 | 2.70 | 2.72 | 0.90 | 0.47 | 0.14 | 0.13 | N/D | N/D | N/D |
| Dimethyl glutarate | 96.81 | 83.91 | 87.38 | 98.11 | 86.81 | 87.64 | 3.34 | 0.40 | 0.21 | N/D |
| Hexane-1,6-diol | 0.05 | 0.06 | 0.06 | 0.06 | 0.05 | 0.06 | N/D | N/D | N/D | 1.14 |
| Di-(5-hydroxypentyl) ether (DHPE) | N/D | N/D | N/D | N/D | N/D | N/D | N/D | N/D | 0.02 | 2.74 |

EXAMPLE 3

The procedure of Example 2 was repeated except that the dimethyl glutarate was supplied to the vaporiser. The results listed in Table 3 were obtained.

TABLE 3

| Fraction | 5 | 10 | 20 | 30 | 40 | 50 | 60 | 70 | Pot |
|---|---|---|---|---|---|---|---|---|---|
| DMG feed rate (ml/h) | 20 | 21 | 0 | 0 | 0 | 0 | 0 | 0 | — |
| Pressure (kPa) | 6.53 | 6.67 | 6.53 | 6.53 | 6.67 | 6.67 | 6.67 | 6.67 | — |
| Reflux ratio | 25:1 | 30:1 | 25:1 | 50:1 | T/R | 40:1 | 23:1 | 30:1 | — |
| Pot (° C.) | 170 | 170 | 173 | 174 | 176 | 178 | 180 | 198 | — |
| Overhead (° C.) | 132 | 142 | 165 | 166 | 167 | 166 | 167 | 166 | — |
| Analysis wt % | | | | | | | | | |
| Butane-1,4-diol | 0.25 | 0.01 | 0.07 | N/D | 0.02 | N/D | N/D | N/D | N/D |
| Pentane-1,5-diol | 2.23 | 14.60 | 88.09 | 98.33 | 98.94 | 99.65 | 99.70 | 99.44 | 75.19 |
| δ-valerolactone | 1.65 | 0.86 | 0.91 | 0.33 | 0.28 | 0.05 | N/D | N/D | N/D |
| Dimethyl glutarate | 94.90 | 83.88 | 9.82 | 0.49 | 0.23 | 0.06 | 0.07 | 0.05 | 0.13 |
| Hexane-1,6-diol | 0.01 | N/D | N/D | N/D | N/D | N/D | N/D | N/D | N/D |
| Di-(5-hydroxypentyl) ether (DHPE) | N/D | N/D | N/D | N/D | N/D | N/D | N/D | 0.26 | 1.3 |

What is claimed is:

1. A process for the continuous recovery of substantially pure pentane-1,5-diol from a crude product stream containing pentane-1,5-diol and δ-valerolactone which comprises:

continuously supplying the feed stream to a vaporisation zone maintained under temperature and pressure conditions effective for the vaporisation of pentane-1,5-diol and conducive to the thermal decomposition of reaction products of δ-valerolactone thereby to form a vaporous stream;

continuously supplying resulting vaporous stream to an intermediate section of a distillation zone, said intermediate section lying below an upper distillation section and above a lower distillation section;

continuously supplying to the upper section of the distillation zone a reflux stream of dimethyl glutarate;

continuously recovering from the upper section of the distillation zone an overhead vapour product stream comprising δ-valerolactone and dimethyl glutarate;

continuously recovering from the distillation zone an intermediate stream comprising substantially pure pentane-1,5-diol; and continuously recovering from the bottom section of the distillation zone a bottoms product.

2. A process according to claim 1, in which the bottoms product is recycled to the vaporisation zone.

3. A process according to claim 1, in which the overhead vaporous stream from the distillation zone is condensed.

4. A process according to claim 1, in which the vaporisation zone and the distillation zone are operated at substantially the same pressure.

5. A process according to claim 4, in which the pressure of operation is atmospheric or sub-atmospheric.

6. A process according to claim 5, in which the pressure of operation is in the range of from 1 kPa up to about 60 kPa.

7. A process according to claim 6, in which the pressure of operation is in the range of from about 2 kPa up to about 20 kPa.

8. A process for the continuous production of pentane-1,5-diol which comprises:

supplying a feed stream comprising dimethyl glutarate in admixture with hydrogen to a hydrogenation zone containing a charge of an ester hydrogenation catalyst maintained under temperature and pressure conditions effective for the hydrogenation of dimethyl glutarate to pentane-1,5-diol;

recovering from the hydrogenation zone a hydrogenation product mixture comprising unreacted hydrogen, methanol, δ-valerolactone and pentane-1,5-diol;

separating from the hydrogenation product mixture a crude reaction product stream comprising δ-valerolactone and pentane-1,5-diol;

continuously supplying the crude reaction product stream to a vaporisation zone maintained under temperature and pressure conditions effective for the vaporisation of pentane-1,5-diol and conducive to the thermal decomposition of reaction products of δ-valerolactone thereby to form a vaporous stream;

continuously supplying resulting vaporous stream to an intermediate section of a distillation zone, said intermediate section lying below an upper distillation section and above a lower distillation section;

continuously supplying to the upper section of the distillation zone a reflux stream of dimethyl glutarate;

continuously recovering from the upper section of the distillation zone an overhead vapour product stream comprising δ-valerolactone and dimethyl glutarate;

continuously recovering from the distillation zone an intermediate stream comprising substantially pure pentane-1,5-diol;

continuously recovering from the bottom section of the distillation zone a bottoms product; and recycling material of the overhead vaporous stream from the distillation zone to the hydrogenation zone.

* * * * *